(12) United States Patent
Choi et al.

(10) Patent No.: US 10,186,035 B2
(45) Date of Patent: Jan. 22, 2019

(54) METHOD AND APPARATUS FOR IMAGE REGISTRATION

(71) Applicant: SAMSUNG MEDISON CO., LTD., Hongcheon-gun (KR)

(72) Inventors: Sung-jin Choi, Hongcheon-gun (KR); Chul-an Kim, Hongcheon-gun (KR); Jae-moon Jo, Hongcheon-gun (KR)

(73) Assignee: SAMSUNG MEDISON CO., LTD., Hongcheon-gun (KR)

( * ) Notice: Subject to any disclaimer, the term of this patent is extended or adjusted under 35 U.S.C. 154(b) by 93 days.

(21) Appl. No.: 15/220,531

(22) Filed: Jul. 27, 2016

(65) Prior Publication Data

US 2017/0200261 A1    Jul. 13, 2017

(30) Foreign Application Priority Data

Jan. 13, 2016    (KR) .................. 10-2016-0004406

(51) Int. Cl.
*G06T 7/00* (2017.01)
*A61B 8/08* (2006.01)
(Continued)

(52) U.S. Cl.
CPC ............ *G06T 7/003* (2013.01); *A61B 8/4263* (2013.01); *A61B 8/463* (2013.01); *A61B 8/5207* (2013.01);
(Continued)

(58) Field of Classification Search
CPC ......... G06T 7/003; G06T 7/33; G06T 7/0012; G06T 7/0044; A61B 8/4263; A61B 8/463; A61B 8/5207; G06F 3/048
See application file for complete search history.

(56) References Cited

U.S. PATENT DOCUMENTS 8,290,303 B2    10/2012    Washburn et al.
8,731,264 B2    5/2014    Kruecker et al.
(Continued)

FOREIGN PATENT DOCUMENTS

EP    2 804 147 A2    11/2014
JP    2003-144412 A    5/2003
(Continued)

OTHER PUBLICATIONS

Communications dated May 9, 2017 by the European Patent Office in counterpart European Patent Application No. 16187543.0.
(Continued)

*Primary Examiner* — Kim Y Vu
*Assistant Examiner* — Molly Delaney
(74) *Attorney, Agent, or Firm* — Sughrue Mion, PLLC (57) ABSTRACT

Provided are an image registration device and an image registration method. The image registration device includes: an ultrasonic image acquirer configured to periodically acquire an ultrasonic image by using a probe of an object; a medical image acquirer configured to acquire a medical image of the object, the medical image having a different modality from the ultrasonic image; a storage unit configured to store pre-acquired ultrasonic images and position information of the probe corresponding to each of the pre-acquired ultrasonic images; and a processor configured to register the ultrasonic image and the medical image, based on a first feature point of the medical image, a second feature point of a first ultrasonic image of the pre-acquired ultrasonic images, and the position information of the probe corresponding to the first ultrasonic image.

13 Claims, 8 Drawing Sheets

(51) Int. Cl.
*A61B 8/00* (2006.01)
*G06F 3/048* (2013.01)
*G06K 9/46* (2006.01)
*G06T 7/33* (2017.01)

(52) U.S. Cl.
CPC ........... *G06F 3/048* (2013.01); *G06K 9/4609* (2013.01); *G06T 7/0012* (2013.01); *G06T 7/0044* (2013.01); *G06T 7/33* (2017.01); *G06T 2207/10081* (2013.01); *G06T 2207/10088* (2013.01); *G06T 2207/10132* (2013.01); *G06T 2207/20092* (2013.01); *G06T 2207/20212* (2013.01); *G06T 2207/30004* (2013.01)

(56) References Cited

U.S. PATENT DOCUMENTS

| | | | |
|---|---|---|---|
| 9,697,634 B2 * | 7/2017 | Dala-Krishna | G06T 13/20 |
| 2011/0178389 A1 | 7/2011 | Kumar et al. | |
| 2011/0306869 A1 | 12/2011 | Hwang et al. | |
| 2014/0321726 A1 * | 10/2014 | Shin | A61B 8/5261 382/131 |
| 2015/0011875 A1 | 1/2015 | Noordhoek et al. | |
| 2015/0178925 A1 | 6/2015 | Jo | |
| 2017/0056057 A1 * | 3/2017 | Thapliyal | A61B 17/320068 |

FOREIGN PATENT DOCUMENTS

| | | |
|---|---|---|
| JP | 3878456 B2 | 2/2007 |
| JP | 5498181 B2 | 5/2014 |
| KR | 10-1118549 B1 | 2/2012 |
| KR | 10-2015-0026354 A | 3/2015 |
| KR | 10-2015-0074304 A | 7/2015 |
| WO | 2008/065600 A2 | 6/2008 |
| WO | 2013/128349 A1 | 9/2013 |

OTHER PUBLICATIONS

Slides from http://graphics.cs.cmu.edu/nsp/course/15-462/Spring04/slides/04-transform.pdf, Carnegie Mellon, Spring 2004, pp. 1-24.

* cited by examiner

METHOD AND APPARATUS FOR IMAGE REGISTRATION

CROSS-REFERENCE TO RELATED APPLICATION

This application claims the benefit of Korean Patent Application No. 10-2016-0004406, filed on Jan. 13, 2016, in the Korean Intellectual Property Office, the disclosure of which is incorporated herein in its entirety by reference.

BACKGROUND

1. Field

One or more embodiments relate to a method and apparatus for image registration.

2. Description of the Related Art

Image registration is a process of representing different images into a common coordinate space by transforming the different images. Image registration may denote reconstruction of at least two images into a single synthesized image. A user may ascertain the correspondence between different images, according to image registration.

In the field of diagnosis based on medical images, image registration is widely used in order to compare images of a diseased body part with each other according to time, to compare images of a diseased body part with each other according to modalities of medical imaging, and to compare an image of a diseased body part with an image of normal tissue. In diagnosis, in order to effectively use an image, which is obtained by increasing strengths of or remedying weaknesses of different image acquisition modalities, image registration is used in which acquired images are represented in a same space to facilitate comparison therebetween.

An image registration method and apparatus capable of quickly providing an accurately registered image is needed by a user to accurately diagnose a disease.

SUMMARY

One or more embodiments include a method and apparatus for image registration between images having different modalities.

Additional aspects will be set forth in part in the description which follows and, in part, will be apparent from the description, or may be learned by practice of the presented embodiments.

According to one or more embodiments, an image registration device includes: an ultrasonic image acquirer configured to periodically acquire an ultrasonic image by using a probe of an object; a medical image acquirer configured to acquire a medical image of the object, the medical image having a different modality from the ultrasonic image; a storage unit configured to store pre-acquired ultrasonic images and position information of the probe corresponding to each of the pre-acquired ultrasonic images; and a processor configured to register the ultrasonic image and the medical image, based on a first feature point of the medical image, a second feature point of a first ultrasonic image of the pre-acquired ultrasonic images, and the position information of the probe corresponding to the first ultrasonic image.

The image registration device may further include a display configured to display the medical image and the pre-acquired ultrasonic images on a screen; and a user input unit configured to receive an input selecting the first feature point of a certain sectional image in the medical image from a user, and receive an input selecting the second feature point of the first ultrasonic image from the user, wherein the processor registers the ultrasonic image and the medical image based on the selected first feature point, the selected second feature point, and the position information of the probe corresponding to the first ultrasonic image.

The processor may determine the position information of the probe corresponding to each of the pre-acquired ultrasonic images, based on information about a point in time at which each of the pre-acquired ultrasonic images is acquired, and information about a point in time at which the position information of the probe is acquired.

The image registration device may further include an instruction unit configured to instruct a user to scan a certain area of the object by using the probe.

The storage unit may store a plurality of ultrasonic images, sectional images in the medical image, which are registered to the plurality of ultrasonic images, respectively, and the position information of the probe corresponding to each of the plurality of ultrasonic images, and the processor may re-register the ultrasonic image and the medical image based on a third feature point of a first sectional image of the sectional images, a fourth feature point of a second ultrasonic image of the plurality of ultrasonic images, and the position information of the probe corresponding to the second ultrasonic image.

The position information of the probe may include information of at least one of a position, a direction, a tilt, and a rotation angle.

The medical image may include a three-dimensional volume image acquired from an external magnetic resonance imaging (MRI) device or an external computed tomography (CT) device.

The first feature point and the second feature point may include areas corresponding to at least one of a portal vein, a branch of a blood vessel, and a tumor of the object.

According to one or more embodiments, an image registration method includes: periodically acquiring an ultrasonic image by using a probe of an object; acquiring a medical image of the object, the medical image having a different modality from the ultrasonic image; storing pre-acquired ultrasonic images and position information of the probe corresponding to each of the pre-acquired ultrasonic images; and registering the ultrasonic image and the medical image, based on a first feature point of the medical image, a second feature point of a first ultrasonic image of the pre-acquired ultrasonic images, and the position information of the probe corresponding to the first ultrasonic image.

According to one or more embodiments, a non-transitory computer-readable recording method has recorded thereon a computer program for executing the image registration method.

BRIEF DESCRIPTION OF THE DRAWINGS

These and/or other aspects will become apparent and more readily appreciated from the following description of the embodiments, taken in conjunction with the accompanying drawings in which.

DETAILED DESCRIPTION

Reference will now be made in detail to embodiments, examples of which are illustrated in the accompanying drawings, wherein like reference numerals refer to like elements throughout. In this regard, the present embodiments may have different forms and should not be construed as being limited to the descriptions set forth herein. Accordingly, the embodiments are merely described below, by referring to the figures, to explain aspects of the present description. As used herein, the term "and/or" includes any and all combinations of one or more of the associated listed items. Expressions such as "at least one of," when preceding a list of elements, modify the entire list of elements and do not modify the individual elements of the list.

In the drawings, parts irrelevant to the description are omitted for simplicity of explanation, and like numbers refer to like elements throughout.

Throughout the specification, when an element is referred to as being "connected" or "coupled" to another element, it can be directly connected or coupled to the other element, or can be electrically connected or coupled to the other element with intervening elements interposed therebetween. In addition, the terms "comprises" and/or "comprising" or "includes" and/or "including" when used in this specification, specify the presence of stated elements, but do not preclude the presence or addition of one or more other elements.

Throughout the specification, a "target object" may denote a living thing or an inanimate object that an image is to represent. The target object may denote the entire or a part of a human body. For example, the target object may be an organ (for example, a liver, a heart, a womb, a brain, a breast, or an abdomen) or a fetus, or may be a cross-section of a human body.

Throughout the specification, a "user" may be a medical expert, such as a doctor, a nurse, a medical technologist, a sonographer, or a medical image expert, but the present invention is not limited thereto. Throughout the specification, an "image" may be an ultrasonic image, a magnetic resonance (MR) image, a computerized tomography (CT) image, a Positron Emission Tomography (PET) image, or the like, but the present invention is not limited thereto.

Throughout the specification, image data may denote a data set from which a medical image can be acquired and may be volume data or two-dimensional (2D) image data.

Volume data may denote a data set of which a basic unit is a voxel and may also denote an image data set including space information together with an anatomical shape of a target object. A voxel denotes a basic unit that defines a three-dimensional (3D) space, together with a pixel serving as a basic unit that defines a point in a 2D cross-section. A voxel may include at least one of a coordinate value, a color value, and a density value.

The present invention will now be described more fully with reference to the accompanying drawings, in which exemplary embodiments of the invention are shown.

Figure 1:
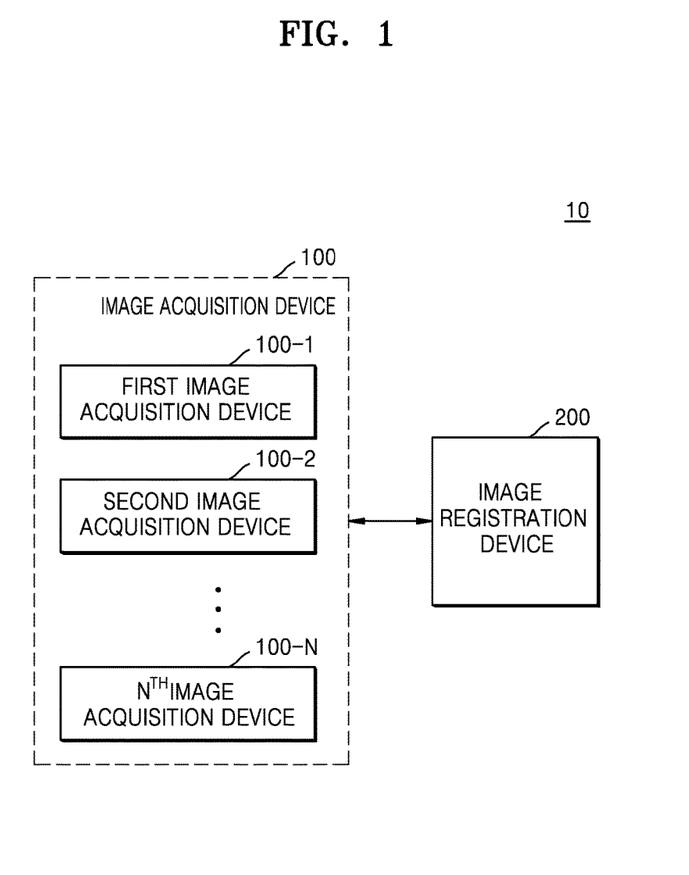
FIG. 1 is a block diagram of an image registration system including an image registration device according to an embodiment.

FIG. 1 is a block diagram of an image registration system 10 including an image registration device 200 according to an embodiment of the present invention.

Referring to FIG. 1, the image registration system 10 according to the present embodiment may include an image acquisition device 100 and the image registration device 200.

The image acquisition device 100 may be an apparatus that acquires a medical image of a target object. For example, the image acquisition device 100 may be a computed tomography (CT) device, a magnetic resonance imaging (MRI) device, an angiography device, an ultrasonic device, or the like, but the present invention is not limited thereto.

Since a CT device is capable of providing a cross-sectional image of a target object, the CT device may express an inner structure (e.g., an organ such as a kidney, a lung, etc.) of the object without an overlap therebetween, compared to a general X-ray capturing apparatus. The CT device may obtain a plurality of images with a thickness not more than 2 mm for several tens to several hundreds of times per second and then may process the plurality of images, thereby providing a relatively accurate cross-sectional image of the target object.

An MRI device is an apparatus for acquiring a sectional image of a part of a target object by expressing, in a contrast comparison, a strength of a MR signal with respect to a radio frequency (RF) signal generated in a magnetic field having a specific strength. For example, if an RF signal that only resonates a specific atomic nucleus (for example, a hydrogen atomic nucleus) is irradiated for an instant onto a target object that lies in a strong magnetic field and then such irradiation stops, an MR signal is emitted from the specific atomic nucleus, and thus the MRI device may receive the MR signal and acquire an MR image from the received MR signal. The MR signal denotes an RF signal emitted from the target object. An intensity of the MR signal may be determined according to a density of a predetermined atom (for example, hydrogen) of the target object, a relaxation time T1, a relaxation time T2, and a flow of blood or the like.

An ultrasonic device transmits an ultrasonic signal toward a certain inner part of a body by using a probe and obtains an image regarding a cross-section of soft tissue or an image regarding blood flow by using information about an ultrasonic signal reflected by the inner part of the body.

The image acquisition device 100 may include a plurality of image acquisition devices. For example, the image acquisition device 100 may include a first image acquisition device 100-1, a second image acquisition device 100-2, . . . , and an N-th image acquisition device 100-N.

The first image acquisition device 100-1 and the second image acquisition device 100-2 may be different types of image acquisition devices using different image acquisition modalities or the same kind of image acquisition devices using the same image acquisition modality.

The image acquisition device 100 may acquire image data about a target object. For example, the first image acquisition device 100-1 may acquire first image data according to a first image acquisition modality, and the second image acquisition device 100-2 may acquire second image data according to a second image acquisition modality. The first image acquisition modality or the second image acquisition modality may be an ultrasonic image acquisition modality, an MR image acquisition modality, a CT image acquisition modality, a PET image acquisition modality, an X-ray image acquisition modality, an optical image acquisition modality, or a combination thereof.

The image registration device 200 may receive a plurality of pieces of image data from the image acquisition device 100 and register the received pieces of image data. The image registration device 200 may perform image registration in consideration of pieces of coordinate information of the plurality of pieces of image data. For example, the image registration device 200 may arrange the pieces of image data so that coordinate systems on which the pieces of image data are formed correspond to each other.

The image registration device 200 may include at least one (for example, the first image acquisition device 100-1) of the first, second, through to N-th image acquisition devices 100-1, 100-2, through to 100-N. In this case, the image registration device 200 may directly acquire a medical image of the target object. For example, when the image registration device 200 includes an ultrasonic device, the image registration device 200 may directly acquire an ultrasound image of the target object. The image registration device 200 may perform registration between the directly acquired ultrasound image and an externally-received or pre-stored CT image.

Figure 2:
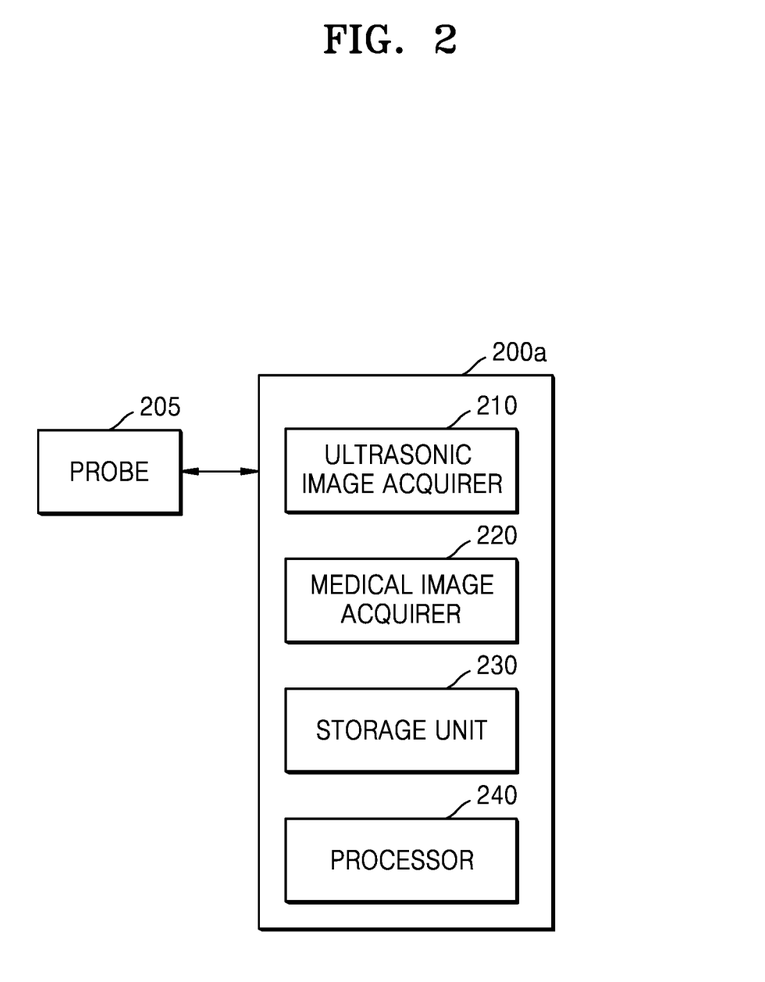
FIG. 2 is a block diagram of an image registration device according to an embodiment.

FIG. 2 is a block diagram of an image registration device 200a according to an embodiment.

The image registration device 200a may include an ultrasonic image acquirer 210, a medical image acquirer 220, a storage unit 230, and a processor 240. The image registration device 200a illustrated in FIG. 2 includes only components thereof according to the present embodiment. Accordingly, it will be understood by one of ordinary skill in the art that other general purpose components than the components illustrated in FIG. 2 may further be included in the image registration device 200a.

The image registration device 200a may be realized as various shapes. For example, the image registration device 200a described in this specification may be realized as a portable terminal as well as a fixed-type terminal. Examples of the portable terminals may include a laptop computer, a personal digital assistant (PDA), a tablet personal computer (PC), etc.

According to an embodiment, the ultrasonic image acquirer 210 may periodically acquire an ultrasonic image with respect to an object by using a probe 205 on the object. According to an embodiment, the ultrasonic image acquirer 210 may be an ultrasonic device including the probe 205. That is, the ultrasonic image acquirer 210 may acquire an ultrasonic image of an object in real time by transmitting and receiving an ultrasonic signal to and from the object, via the probe 205. Also, according to another embodiment, the ultrasonic image acquirer 210 may periodically acquire an ultrasonic image of an object, from an external ultrasonic device including the probe 205. Also, according to an embodiment, the ultrasonic image acquirer 210 may acquire position information of the probe 205 corresponding to an ultrasonic image.

According to an embodiment, the medical image acquirer 220 may acquire a medical image of an object having a different modality from the ultrasonic image. According to an embodiment, the medical image may be a 3D volume image of an object. For example, the medical image of the object having a different modality from the ultrasonic image may be a CT image or an MR image of the object. According to an embodiment, the medical image acquirer 220 may acquire the medical image of the object from an external CT device or an external MR image device. Alternatively, the medical image acquirer 220 may acquire a pre-stored medical image of an object from an external storage medium. Also, the medical image acquirer 220 may acquire a CT image or an MR image stored in a server via a network, by using a picture archiving and communication system (PACS).

According to an embodiment, the storage unit 230 may store ultrasonic images pre-acquired by the ultrasonic image acquirer 210, and position information of the probe 205 corresponding to each of the ultrasonic images. Also, the storage unit 230 may store the pre-acquired ultrasonic images and the position information of the probe 205 for acquiring each of the ultrasonic images such that the pre-acquired ultrasonic images correspond to the position information of the probe 205 for acquiring each of the ultrasonic images. For example, the storage unit 230 may store a first ultrasonic image of the ultrasonic images and the position information of the probe 205 corresponding to the first ultrasonic image. According to an embodiment, the position information of the probe 205 may include information of at least one of a position, a direction, a tilt, and a rotation angle of the probe 205. According to an embodiment, the position information of the probe 205 may be acquired by a device (not shown) for tracking a position of the probe 205.

The storage unit 230 may include at least one type of storage medium from a flash memory type, a hard disk type, a multimedia card micro type, a card type memory (for example, an SD memory, an XD memory, etc.), random access memory (RAM), static random access memory (SRAM), read-only memory (ROM), electrically erasable programmable read-only memory (EEPROM), programmable read-only memory (PROM), magnetic memory, a magnetic disk, and an optical disk. Also, the image registration device 200a may run a web storage or a cloud server on the internet which performs a storage function of the storage unit 230.

According to an embodiment, the processor 240 may register the ultrasonic image and the medical image based on a first feature point of the medical image, a second feature point of the first ultrasonic image of the pre-stored ultrasonic images, and the position information of the probe corresponding to the first ultrasonic image. According to an embodiment, the information of the first feature point of the medical image, the first ultrasonic image, and the second feature point of the first ultrasonic image may be input from a user.

A feature point may be a certain point, line, region, or volume serving as a basis for distinguishing parts of a target object from each other. For example, the feature point be a hepatic vein, a portal vein, or an inferior vena cava (IVC) of a liver, an outline of the liver, a branch area of a blood vessel of a kidney, an area in which lacteal gland of a breast is divided, a nipple, a carotid of thyroid, muscle or tendon of a musculoskeletal system, or a tumor. Thus, according to an embodiment, the image registration device 200a may select, as a feature point, a region corresponding to the IVC and the portal vein within volume data for a liver. Also, the feature point may serve as a basis for registration between pieces of image data. For example, the feature point may be a region that can be an anatomical feature, or a region corresponding to a target tumor.

In more detail, the processor 240 may acquire a transformation matrix which makes a coordinate system of the ultrasonic image correspond to a coordinate system of the medical image, based on the first feature point of a certain section of the medical image, the second feature point of the first ultrasonic image of the ultrasonic images, and the position information of the probe corresponding to the first ultrasonic image. Also, based on the acquired transformation matrix, the processor 240 may register the periodically acquired ultrasonic image and the medical image. According to an embodiment, the ultrasonic image and the medical image may use a coordinate system according to digital imaging and communication in medicine (DICOM).

According to an embodiment, the processor 240 may set a reference coordinate system and transform the coordinate system of the ultrasonic image into the reference coordinate system. For example, the reference coordinate system may denote a coordinate system which is set, with a position of a tracker (not shown) configured to generate an electromagnetic wave in order to track the probe 25, as an original point. Thus, the processor 240 may acquire position information of the probe 205 tracked by the tracker on the reference coordinate system. Also, the processor 240 may represent a sectional image in the medical image, on a DICOM coordinate system which may be formed in coronal, sagittal, and axial directions. Also, the processor 240 may acquire a rotational transformation matrix for transforming the reference coordinate system into the DICOM coordinate system.

Next, the processor 240 may transform a coordinate of the first feature point of the medical image into a coordinate on the DICOM coordinate system. Also, the processor 240 may convert a coordinate of the second feature point of the first ultrasonic image of the ultrasonic images into a coordinate on the reference coordinate system, by using the position information of the probe 205. Next, the processor 240 may acquire a movement transformation matrix for transforming the reference coordinate system into the DICOM coordinate system. In order to acquire the movement transformation matrix, the processor 240 may calculate a difference between the coordinate of the first feature point on the DICOM coordinate system and the coordinate of the second feature point on the reference coordinate system. Thus, the processor 240 may acquire the transformation matrix based on the first feature point of the certain section in the medical image, the second feature point of the first ultrasonic image of the ultrasonic images, and the position information of the probe corresponding to the first ultrasonic image. Also, based on the acquired transformation matrix, the processor 240 may register the medical image to the periodically acquired ultrasonic image in real time.

Thus, when the user is to register the ultrasonic image acquired by using the probe 205 and the medical image having a different modality from the ultrasonic image, the user may search for a desired feature point in the ultrasonic images that are pre-stored in the storage unit 230. Thus, the user may more conveniently select the feature point. In addition, when the user selects the feature point in the ultrasonic image stored in the storage unit 230, the user may freely select the desired feature point, since the storage unit 230 also stores position information of the ultrasonic image.

Also, according to an embodiment, the processor 240 may perform re-registration based on the registered ultrasonic image and medical image. For example, inaccurate registration may be performed, when a coordinate system is changed due to motion of an object, such as breathing, or when there is a selection error with respect to a plurality of feature points. Also, when an object is a large organ, such as a liver, it may be difficult to acquire an ultrasonic image of the whole object by one time ultrasonic scan, and thus, an anatomical positional error may occur in selecting a feature point, and thus, a registration error may be caused. That is, a registration error between an ultrasonic image and a medical image may occur. Accordingly, the processor 240 may perform re-registration. Also, the processor 240 may perform initial registration with respect to an organ, such as a blood vessel, in which a feature point may be relatively accurately selected, and may perform re-registration by selecting another feature point with respect to a peripheral object. Hereinafter, the processor 240 performing re-registration will be described.

The processor 240 may periodically acquire a plurality of ultrasonic images and sectional images in the medical image, which are registered to the plurality of ultrasonic images, respectively.

The storage unit 230 may store the plurality of ultrasonic images, the sectional images in the medical image, which are registered to the plurality of ultrasonic images, respectively, and the position information of the probe corresponding to each of the plurality of ultrasonic images. That is, the storage unit 230 may store the periodically acquired plurality of registered ultrasonic images and sectional images, and the position information of the probe 205 for acquiring each of the plurality of registered ultrasonic images and sectional images such that the periodically acquired plurality of registered ultrasonic images and sectional images correspond to the position information of the probe 205 for acquiring each of the plurality of registered ultrasonic images and sectional images.

Next, the processor 240 may re-register the ultrasonic image and the medical image, based on a third feature point of a first sectional image of the sectional images of the medical image stored in the storage unit 230, a fourth feature point of a second ultrasonic image of the plurality of ultrasonic images, and the position information of the probe 205 corresponding to the second ultrasonic image. That is, the processor 240 may re-set a transformation function, when the third feature point and the fourth feature point are re-selected, and may re-register the ultrasonic image and the medical image according to the re-set transformation function. According to an embodiment, the third feature point of the first sectional image, the second ultrasonic image, and the fourth feature point of the second ultrasonic image may be selected by a user. More detailed aspects will be described later with reference to FIG. 6.

Also, according to an embodiment, the processor 240 may acquire information about a point in time at which the ultrasonic images are acquired, and information about a point of time at which the position information of the probe 205 is acquired. Also, the storage unit 230 may store the information about the point in time at which the ultrasonic images are acquired, and the information about the point in time at which the position information of the probe 205 is acquired.

Next, the processor 240 may determine the position information of the probe 205 more accurately corresponding to each of the ultrasonic images, by using the information about the point in time at which the ultrasonic images are acquired, and the information about the point in time at which the position information of the probe 205 is acquired. More detailed aspects will be described later with reference to FIG. 3.

Figure 3:
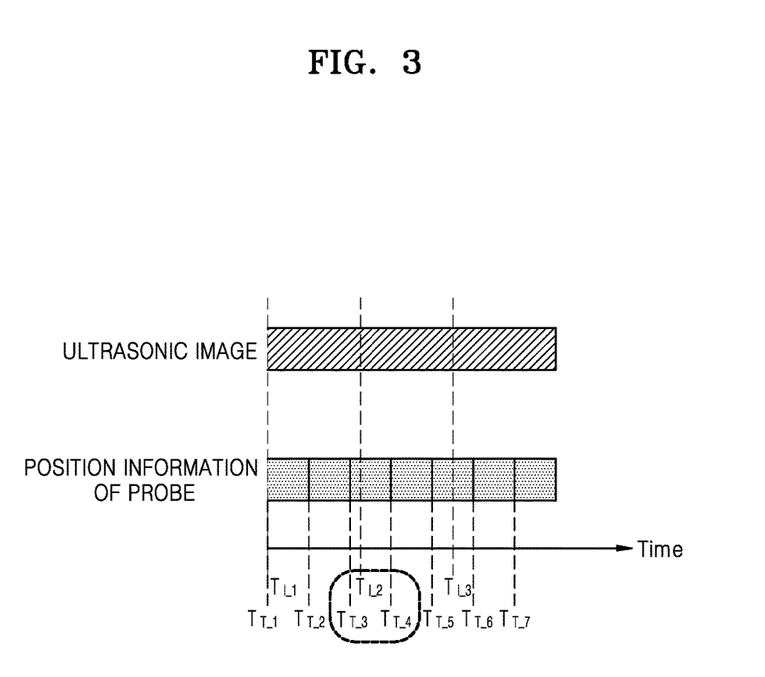
FIG. 3 is a view for describing an embodiment in which an image registration device determines position information of a probe corresponding to an ultrasonic image.

FIG. 3 is a view for describing an embodiment in which the image registration device determines the position information of the probe corresponding to an ultrasonic image.

According to an embodiment, the processor 240 may acquire information about points in time TI_1, TI_2, and TI_3, at which ultrasonic images are acquired. Also, the processor 240 may acquire information about points in time TT_1, TT_2, TT_3, TT_4, TT_5, TT_6, and TT_7, at which position information of the probe is acquired. Hereinafter, for convenience of explanation, the position information of the probe acquired at the point in time TT_1 will be referred to as Tprobetotracker (TT_1).

As illustrated in FIG. 3, since the points in time TI_1 and TT_1 are the same points in time, the processor 240 may determine the position information of the probe corresponding to the ultrasonic image acquired at the point in time TI_1 as Tprobetotracker (TT_1). However, since although an ultrasonic image acquired at the point in time TI_2 exists, the position information of the probe acquired at the point in time TI_2 does not exist, the processor 240 may determine the position information of the probe corresponding to the ultrasonic image acquired at the point in time TI_2, based on Tprobetotracker (TT_3) and Tprobetotracker (TT_4). According to an embodiment, the processor 240 may perform interpolation with respect to Tprobetotracker (TT_3) and Tprobetotracker (TT_4) to determine the position information of the probe corresponding to the ultrasonic image acquired at time point in time TI_2.

Figure 4:
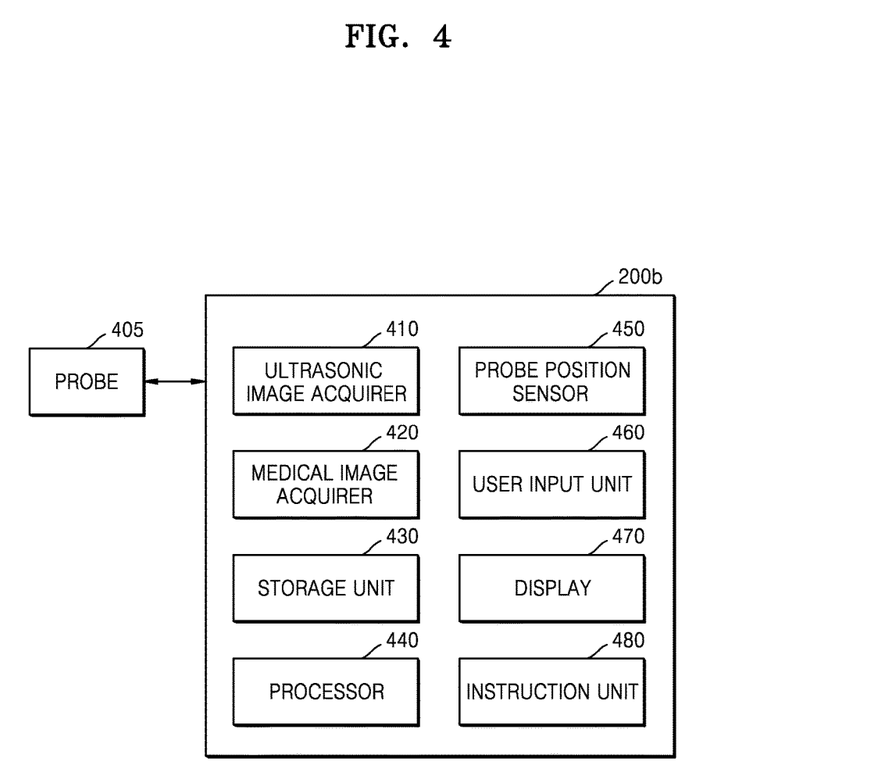
FIG. 4 is a block diagram of an image registration device according to an embodiment.

FIG. 4 is a block diagram of an image registration device 200b according to an embodiment.

The image registration device 200b may include an ultrasonic image acquirer 410, a medical image acquirer 420, a storage unit 430, a processor 440, a probe position sensor 450, a user input unit 460, a display 470, and an instruction unit 480. The image registration device 200b illustrated in FIG. 4 includes only components thereof according to the present embodiment. Accordingly, it will be understood by one of ordinary skill in the art that other general purpose components than the components illustrated in FIG. 4 may further be included in the image registration device 200b.

The ultrasonic image acquirer 410, the medical image acquirer 420, the storage unit 430, and the processor 440 of FIG. 4 correspond to the ultrasonic image acquirer 210, the medical image acquirer 220, the storage unit 230, and the processor 240, and thus, their descriptions will not be repeated.

The probe position sensor 450 may detect position information of the probe 405. The position information of the probe 405 may include information of at least one of a position, a direction, a tilt, and a rotation angle of the probe 405. According to an embodiment, the probe position sensor 450 may be included in the probe 405, or may include a sensor bonded to the probe 405, such as a tilt sensor, etc.

Also, the probe position sensor 450 may be located outside the image registration device 200b. The probe position sensor 450 located outside the image registration device 200b may be located in a shielded room in which an image of an object is photographed. Methods in which the probe position sensor 450 detects the position of the probe 405 may include a method using an electromagnetic field, a method using a laser, etc., a method using a depth camera, a method of using a combination of an acceleration sensor and a gravity sensor, etc.

The user input unit 460 may receive an input selecting a first feature point of a medical image acquired by the medical image acquirer 420, from a user. That is, the user may search for a medical image and select the first feature point of a sectional image in the medical image, via the user input unit 460. Also, the user input unit 460 may receive an input selecting a second feature point of a first ultrasonic image of ultrasonic images stored in the storage unit 430, from the user. That is, the user may select the first ultrasonic image of the ultrasonic images stored in the storage unit 430 and select the second feature point of the first ultrasonic image via the user input unit 460.

The user input unit 460 may include, but is not limited to, a key pad, a dome switch, a touch pad (e.g., a capacitive overlay type, a resistive overlay type, an infrared beam type, an integral strain gauge type, a surface acoustic wave type, a piezoelectric type, or the like), a jog wheel, or a jog switch. In particular, as described above, when a touch pad forms a layer structure together with a display panel, the user input unit 460 may be referred to as a touch screen.

The display 470 may display an ultrasonic image acquired by the ultrasonic image acquirer 410 or a medical image acquired by the medical image acquirer 420 on a screen. Also, the display 470 may display information processed by the image registration device 200b. For example, the display unit 470 may display state information which is necessary for acquiring and registering images, a user interface (UI) or a graphic user interface (GUI) related to function setting, and an image about an object. Also, when the display panel forms the layer structure together with the touch pad, and the touch screen is formed, the display 470 may also be used as an input device in addition to an output device.

Also, the display 470 may display an ultrasonic image and a medical image which are registered by the processor 440 on the screen.

The display 470 may include at least one of a liquid crystal display, a thin film transistor-liquid crystal display, an organic light-emitting diode, a flexible display, a 3D display, and an electrophoretic display.

The instruction unit 480 may instruct a user to scan a certain area of an object via the probe 405. That is, the instruction unit 480 may instruct the user to scan a certain area of the object via the probe 405, in order to acquire an ultrasonic image of an area which may be easily registered. For example, the instruction unit 480 may instruct the user to scan a hepatic portal vein area of a human body, via a sound. Also, according to another embodiment, the instruction unit 480 may display an instruction to scan a branch area of a blood vessel of the human body on the screen to instruct the user. Thus, the user may scan the area which may be easily registered via the probe 405, and the scan result storage unit 430 may store at least one ultrasonic image with respect to the area which may be easily registered. Thus, the user may more easily select an ultrasonic image and a feature point for registration, from among the at least one ultrasonic image stored in the storage unit 430.

Figure 5:
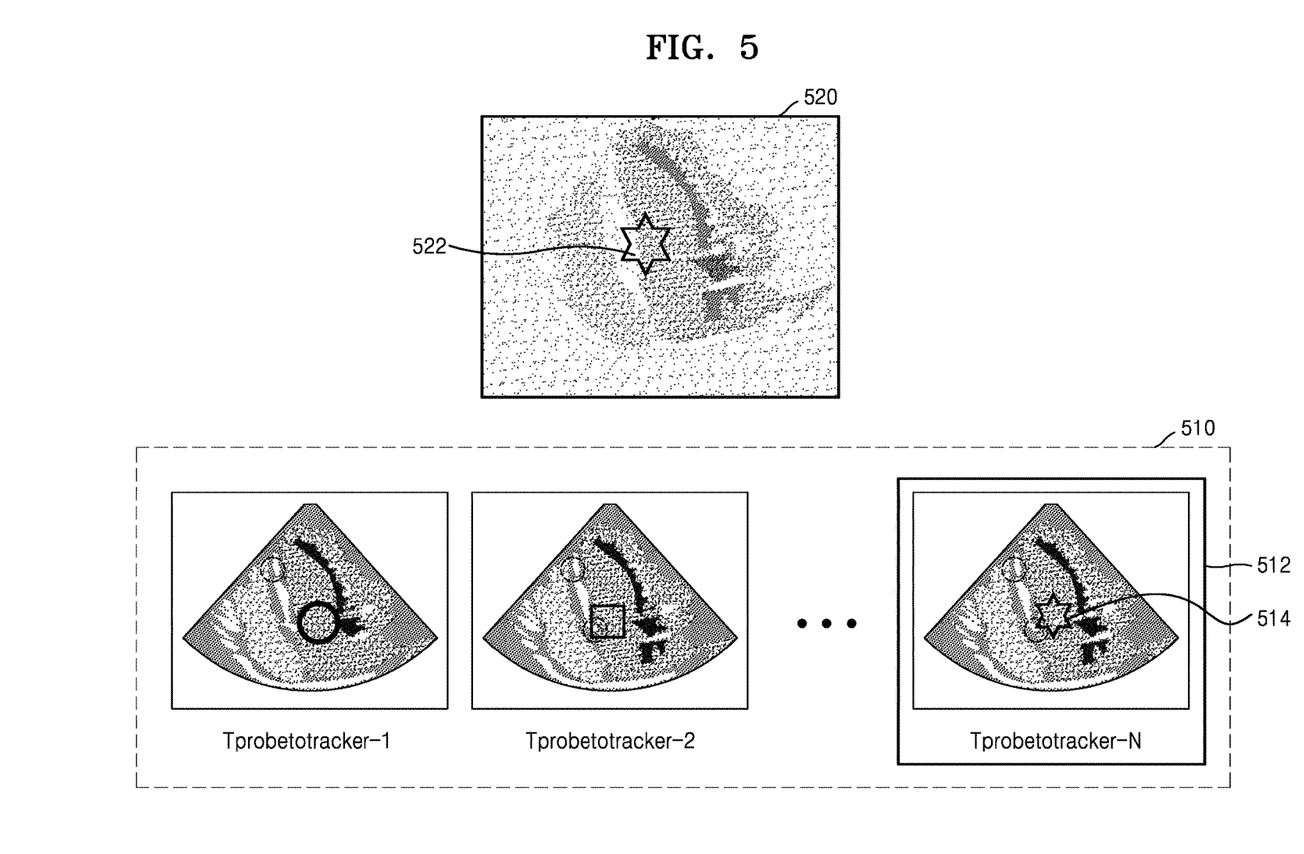
FIG. 5 is a view for describing an embodiment in which a processor registers an ultrasonic image and a medical image based on stored ultrasonic images and position information of a probe.

FIG. 5 is a view for describing an embodiment in which the processor 220 or 440 registers an ultrasonic image and a medical image based on ultrasonic images and position information of the probe that are stored.

The storage unit 230 or 430 may store pre-acquired ultrasonic images 510 and position information of the probe Tprobetotracker-1, Tprobetotracker-2, and Tprobetotracker-N corresponding to each of the pre-acquired ultrasonic images 510.

A user may search for a medical image pre-acquired by the medical image acquirer 220 or 420 and may select a first feature point 522 indicated in a sectional image 520 in the medical image. According to an embodiment, the display 470 may display the medical image on a screen, and the user input unit 460 may receive an input selecting the first feature point 522 of the sectional image 520 in the medical image.

Next, the user may select a second feature point 514 which may correspond to the first feature point 522 from a first ultrasonic image 512 of the pre-stored ultrasonic images 510. According to an embodiment, the display 470 may display the ultrasonic images 510, and the user may select the first ultrasonic image 512 indicating a second feature point 514 from the ultrasonic images 510, and my select the first feature point 522 of the first ultrasonic image 512. According to an embodiment, the user input unit 460 may receive an input selecting the second feature point 514 of the first ultrasonic image 512.

Thus, the processor 240 or 440 may register the ultrasonic image and the medical image based on the first feature point 522, the second feature point 514, and the position information of the probe Tprobetotracker-N corresponding to the first ultrasonic image 512.

In FIG. 5, it is described that after the first feature point 522 of the medical image is selected, the second feature point 514 of the first medical image 512 is selected. However, it is not limited thereto. According to another embodiment, after the second feature point 514 is selected, the first feature point 522 may be selected.

Figure 6:
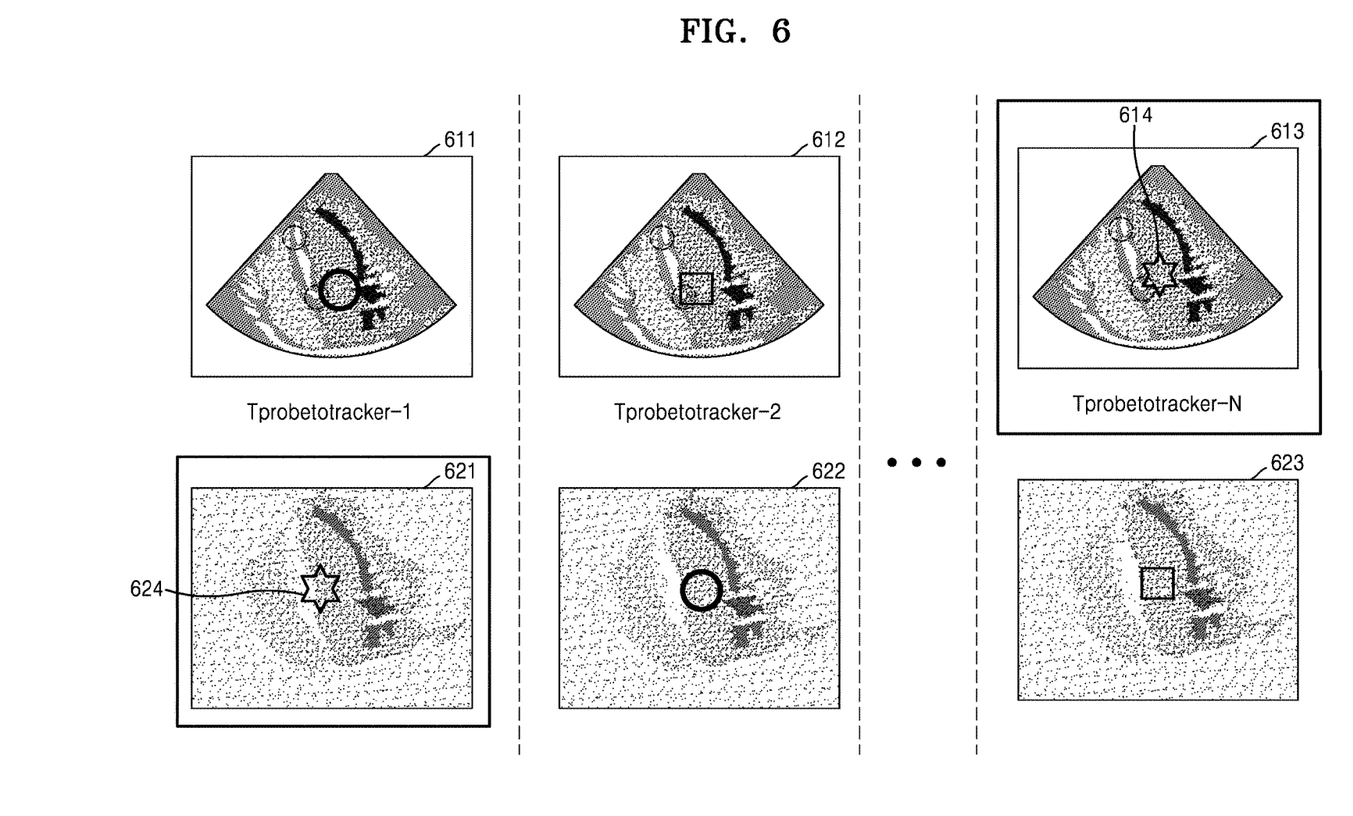
FIG. 6 is a view for describing an embodiment in which a processor re-registers an ultrasonic image and a medical image.

FIG. 6 is a view for describing an embodiment in which the processor 240 or 440 re-registers an ultrasonic image and a medical image.

The processor 240 or 440 may acquire a plurality of ultrasonic images 611, 612, and 613, and sectional images 621, 622, and 623 in a medical image, which are registered to the plurality of ultrasonic images 611, 612, and 613, respectively.

Next, the storage unit 230 or 430 may store the plurality of ultrasonic images 611, 612, and 613, the sectional images 621, 622, and 623, and position information of the probe Tprobetotracker-1, Tprobetotracker-2, and Tprobetotracker-N corresponding to the plurality of ultrasonic images 611, 612, and 613, respectively.

A user may search for the sectional images 621, 622, and 623 and may select a third feature point 624 indicated in the first sectional image 621 of the sectional images 621, 622, and 623. According to an embodiment, the display 470 may display the sectional images 621, 622, and 623 on a screen, and the user input unit 460 may receive an input selecting the third feature point 624 of the first sectional image 621 of the sectional images 621, 622, and 623.

Next, the user may select a fourth feature point 614 which may correspond to the third feature point 624 from the second ultrasonic image 613 of the plurality of ultrasonic images 611, 612, and 613. According to an embodiment, the display 470 may display the plurality of ultrasonic images 611, 612, and 613, and the user may select the second ultrasonic image 613 indicating the fourth feature point 614 from among the plurality of ultrasonic images 611, 612, and 613, and may select the fourth feature point 614 of the second ultrasonic image 613. According to an embodiment, the user input unit 460 may receive an input selecting the fourth feature point 614 of the second ultrasonic image 613.

Thus, the processor 240 or 440 may re-register the ultrasonic image and the medical image based on the third feature point 624 of the first sectional image 621, the fourth feature point 614 of the second ultrasonic image 613, and the position information of the probe Tprobetotracker-N corresponding to the second ultrasonic image 613.

In FIG. 6, it is described that after the third feature point 624 of the first sectional image is selected, the fourth feature point 614 of the second ultrasonic image 613 is selected. However, it is not limited thereto. According to another embodiment, after the fourth feature point 614 is selected, the third feature point 624 may be selected.

Figure 7:
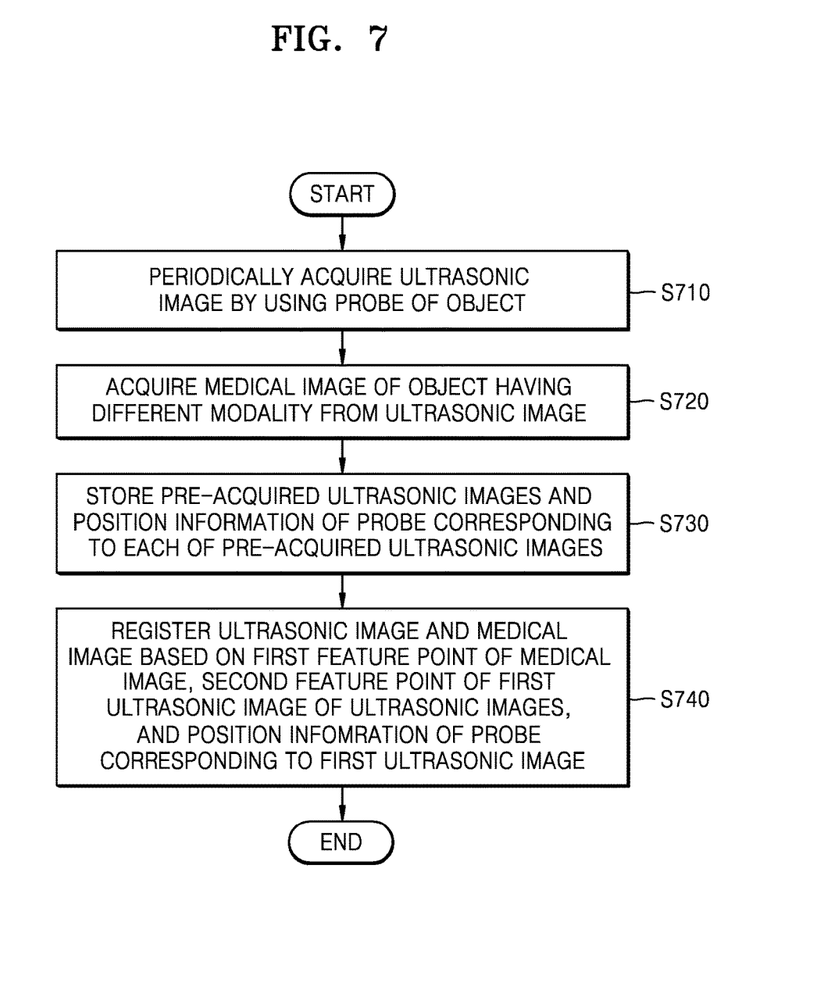
FIG. 7 is a flowchart of an image registration method according to an embodiment.

FIG. 7 illustrates an image registration method according to an embodiment.

The method illustrated in FIG. 7 may be performed by the image registration devices 200, 200a, and 200b of FIGS. 1, 2, and 4. Repeated descriptions will be omitted.

In operation S710, the image registration device 200, 200a, or 200b may periodically acquire an ultrasonic image by using a probe on an object. That is, the image registration device 200, 200a, or 200b may transmit and receive ultrasonic signals to and from the object via the probe, and may acquire an ultrasonic image of the object in real time. Also, according to another embodiment, the image registration device 200, 200a, or 200b may periodically acquire an ultrasonic image of an object, from an external ultrasonic device including a probe. Also, the image registration device 200, 200a, or 200b may acquire the ultrasonic image and position information of the probe corresponding to the ultrasonic image. Also, according to an embodiment, the image registration device 200, 200a, or 200b may instruct a user to scan a certain area of the object via the probe. That is, the image registration device 200, 200a, or 200b may instruct the user to scan a certain area of the object via the probe, in order to acquire an ultrasonic image with respect to an area which may be easily registered. For example, the image registration device 200, 200a, or 200b may instruct the user to scan a hepatic portal vein area on a human body, via a sound. Also, according to another embodiment, the image registration device 200, 200a, or 200b may instruct the user by displaying an instruction to scan a branch area of a blood vessel of the human body In operation S720, the image registration device 200, 200a, or 200b may acquire a medical image of the object having a different modality from the ultrasonic image. According to an embodiment, the medical image may be a 3D volume image of the object. For example, the medical image of the object having the different modality from the ultrasonic image may be a CT image or an MR image of the object. According to an embodiment, the image registration device 200, 200a, or 200b may acquire the medical image of the object from an external CT image device or MR image device, or may acquire the pre-stored medical image of the object from an external storing medium.

According to an embodiment, the image registration device 200, 200a, or 200b may store pre-acquired ultrasonic images and position information of the probe corresponding to each of the ultrasonic images. Also, the image registration device 200, 200a, or 200b may store the pre-acquired ultrasonic images and the position information of the probe for acquiring each of the ultrasonic images such that the pre-acquired ultrasonic images correspond to the position information of the probe for acquiring each of the ultrasonic images. For example, the image registration device 200, 200a, or 200b may store a first ultrasonic image of the ultrasonic images and the position information of the probe 205 corresponding to the first ultrasonic image. According to an embodiment, the position information of the probe may include information of at least one of a position, a direction, a tilt, and a rotation angle of the probe 205.

Also, according to an embodiment, the image registration device 200, 200a, or 200b may acquire information about a point in time at which the ultrasonic images are acquired, and information about a point of time at which the position information of the probe is acquired. Also, the image registration device 200, 200a, or 200b may store the information about the point in time at which the ultrasonic images are acquired, and the information about the point in time at which the position information of the probe is acquired.

Next, the image registration device 200, 200a, or 200b may determine the position information of the probe more accurately corresponding to each of the ultrasonic images, by using the information about the point in time at which the ultrasonic images are acquired, and the information about the point in time at which the position information of the probe is acquired.

According to an embodiment, the image registration device 200, 200a, or 200b may display the acquired ultrasonic image or the acquired medical image on a screen. Also, the image registration device 200, 200a, or 200b may display information processed by the image registration device 200, 200a, or 200b.

In operation S740, the image registration device 200, 200a, or 200b may register the ultrasonic image and the medical image based on a first feature point of the medical image, a second feature point of a first ultrasonic image of the ultrasonic images, and position information of the probe corresponding to the first ultrasonic image. According to an embodiment, information of the first feature point of the medical image, the first ultrasonic image, and the second feature point of the first ultrasonic image may be input from a user. That is, the user may select the first feature point of a sectional image in the medical image by searching for the medical image via the image registration device 200, 200a, or 200b. Also, the user may select the first ultrasonic image from among the pre-stored ultrasonic images and may select the second feature point of the first ultrasonic image, via the image registration device 200, 200a, or 200b.

In more detail, the image registration device 200, 200a, or 200b may acquire a transformation matrix that makes a coordinate system of the ultrasonic image and a coordinate system of the medical image correspond to each other, based on the first feature point of the certain section of the medical image, the second feature point of the first ultrasonic image of the ultrasonic images, and the position information of the probe corresponding to the first ultrasonic image. Also, the image registration device 200, 200a, or 200b may register the periodically acquired ultrasonic image and the medical image, based on the acquired transformation matrix.

Figure 8:
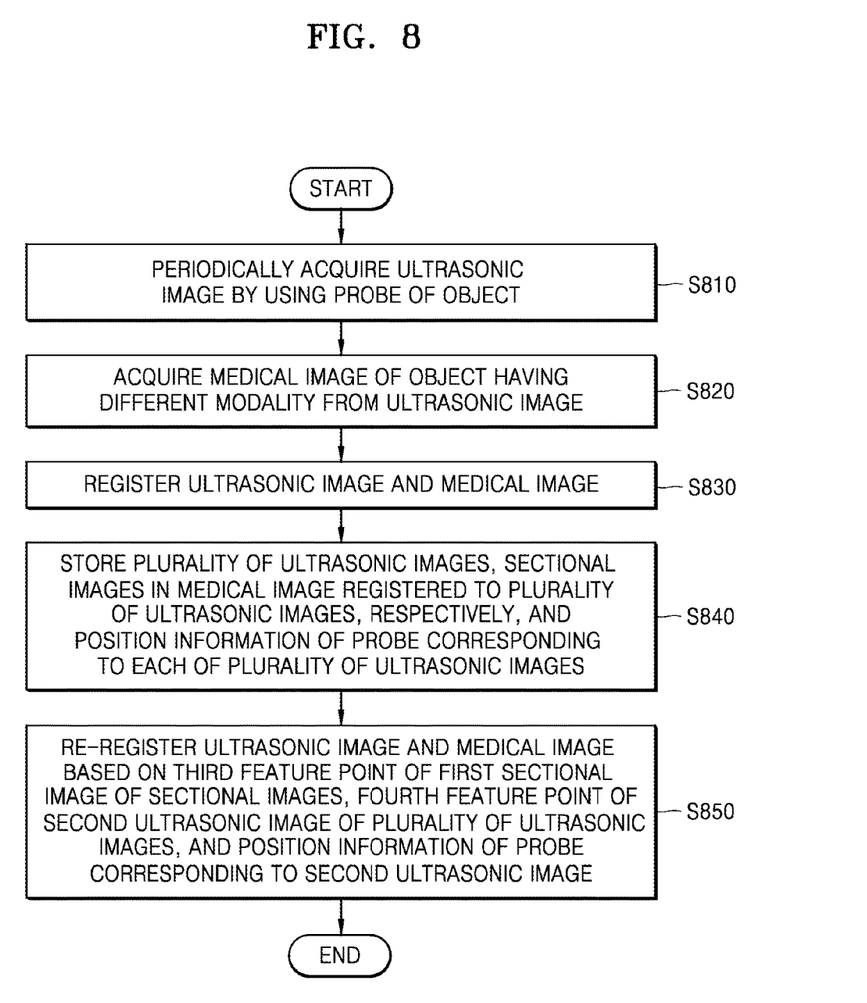
FIG. 8 is a flowchart of an image registration method according to another embodiment.

FIG. 8 illustrates an image registration method according to another embodiment.

The method illustrated in FIG. 8 may be performed by the image registration devices 200, 200a, and 200b of FIGS. 1, 2, and 4. Repeated descriptions will be omitted.

In operation S810, the image registration device 200, 200a, or 200b may periodically acquire an ultrasonic image by using a probe on an object. Operation S810 corresponds to operation S710, and thus, repeated descriptions will be omitted.

In operation S820, the image registration device 200, 200a, or 200b may acquire a medical image of the object having a different modality from the ultrasonic image. Operation S820 corresponds to operation S720, and thus, repeated descriptions will be omitted.

In operation S830, the image registration device 200, 200a, or 200b may register the ultrasonic image and the medical image. According to an embodiment, the image registration device 200, 200a, or 200b may acquire a transformation matrix that makes a coordinate system of the ultrasonic image correspond to a coordinate system of the medical image, and may register the periodically acquired ultrasonic image and the medical image based on the acquired transformation matrix.

In operation S840, the image registration device 200, 200a, or 200b may store a plurality of ultrasonic images, sectional images in the medical image which are registered to the plurality of ultrasonic images, respectively, and the position information of the probe corresponding to each of the plurality of ultrasonic images. That is, the image registration device 200, 200a, or 200b may store the periodically acquired plurality of registered ultrasonic images and sectional images, and the position information of the probe for acquiring each of the plurality of registered ultrasonic images and sectional images such that the periodically acquired plurality of registered ultrasonic images and sectional images correspond to the position information of the probe for acquiring each of the plurality of registered ultrasonic images and sectional images.

In operation S850, the image registration device 200, 200a, or 200b may re-register the ultrasonic image and the medical image based on a third feature point of a first sectional image of the sectional images, a fourth feature point of a second ultrasonic image of the plurality of ultrasonic images, and the position and direction information of the probe corresponding to the second ultrasonic image. According to an embodiment, the third feature point of the first sectional image, the second ultrasonic image, and the fourth feature point of the second ultrasonic image may be selected by a user.

The device described herein may comprise a processor, a memory for storing program data and executing it, a permanent storage unit such as a disk drive, a communication port for handling communications with external devices, and user interface devices such as a touch panel, a key, a button, etc. Any processes may be implemented as software modules or algorithms, and may be stored as program instructions or computer readable codes executable by a processor on a computer-readable media such as read-only memory (ROM), random-access memory (RAM), CD-ROMs, magnetic tapes, floppy disks, and optical data storage unit devices. The computer readable recording medium can also be distributed over network coupled computer systems so that the computer readable code is stored and executed in a distributed fashion. This media can be read by the computer, stored in the memory, and executed by the processor.

The present inventive concept may be described in terms of functional block components and various processing steps. Such functional blocks may be realized by any number of hardware and/or software components configured to perform the specified functions. For example, the present inventive concept may employ various integrated circuit components, e.g., memory elements, processing elements, logic elements, look-up tables, and the like, which may carry out a variety of functions under the control of one or more microprocessors or other control devices. Similarly, where the elements of the present inventive concept are implemented using software programming or software elements the inventive concept may be implemented with any programming or scripting language such as C, C++, Java, assembler, or the like, with the various algorithms being implemented with any combination of data structures, objects, processes, routines or other programming elements. Functional aspects may be implemented in algorithms that execute on one or more processors. Furthermore, the present inventive concept could employ any number of conventional techniques for electronics configuration, signal processing and/or control, data processing and the like. The words "mechanism" and "element" are used broadly and are not limited to mechanical or physical embodiments, but can include software routines in conjunction with processors, etc.

The particular implementations shown and described herein are illustrative examples of the inventive concept and are not intended to otherwise limit the scope of the inventive concept in any way. For the sake of brevity, conventional electronics, control systems, software development and other functional aspects of the systems (and components of the individual operating components of the systems) may not be described in detail. Furthermore, the connecting lines, or connectors shown in the various figures presented are intended to represent exemplary functional relationships and/or physical or logical couplings between the various elements. It should be noted that many alternative or additional functional relationships, physical connections or logical connections may be present in a practical device.

The use of the terms "a" and "an" and "the" and similar referents in the context of describing the inventive concept (especially in the context of the following claims) are to be construed to cover both the singular and the plural. Furthermore, recitation of ranges of values herein are merely intended to serve as a shorthand method of referring individually to each separate value falling within the range, unless otherwise indicated herein, and each separate value is incorporated into the specification as if it were individually recited herein. Finally, the steps of all methods described herein can be performed in any suitable order unless otherwise indicated herein or otherwise clearly contradicted by context. The use of any and all examples, or exemplary language (e.g., "such as") provided herein, is intended merely to better illuminate the inventive concept and does not pose a limitation on the scope of the inventive concept unless otherwise claimed. Numerous modifications and adaptations will be readily apparent to those of ordinary skill in this art without departing from the spirit and scope of the present inventive concept.

It should be understood that embodiments described herein should be considered in a descriptive sense only and not for purposes of limitation. Descriptions of features or aspects within each embodiment should typically be considered as available for other similar features or aspects in other embodiments.

While one or more embodiments have been described with reference to the figures, it will be understood by those of ordinary skill in the art that various changes in form and details may be made therein without departing from the spirit and scope of the inventive concept as defined by the following claims.

What is claimed is:

1. An image registration device comprising:
    an ultrasonic image acquirer including a probe configured to periodically acquire ultrasonic images by using the probe, of an object;
    a medical image acquirer configured to acquire a medical image of the object from an external medical image device, the medical image having a different modality from the ultrasonic image;
    a memory configured to store pre-acquired ultrasonic images and position information of the probe corresponding to each of the pre-acquired ultrasonic images;
    a display screen configured to display the medical image and the pre-acquired ultrasonic images;
    a user input device configured to receive an input selecting a first feature point of the medical image, and receive an input selecting a second feature point of a first ultrasonic image among the stored pre-acquired ultrasonic images; and
    a processor configured to register the first ultrasonic image and the medical image, based on the first feature point of the medical image, the second feature point of the first ultrasonic image, and the position information of the probe corresponding to the first ultrasonic image, wherein the stored position information of the probe is determined by the processor, based on information about a point in time at which each of the pre-acquired ultrasonic images is acquired, and information about a point in time at which the position information of the probe is acquired.

2. The image registration device of claim 1, further comprising an instruction unit configured to instruct a user to scan a certain area of the object by using the probe.

3. The image registration device of claim 1, wherein the memory stores a plurality of ultrasonic images, sectional images in the medical image, which are registered to the plurality of ultrasonic images, respectively, and the position information of the probe corresponding to each of the plurality of ultrasonic images, and
    the processor re-registers the ultrasonic image and the medical image based on a third feature point of a first sectional image of the sectional images, a fourth feature point of a second ultrasonic image of the plurality of ultrasonic images, and the position information of the probe corresponding to the second ultrasonic image.

4. The image registration device of claim 1, wherein the position information of the probe comprises information of at least one of a position, a direction, a tilt, and a rotation angle.

5. The image registration device of claim 1, wherein the medical image comprises a three-dimensional volume image acquired from an external magnetic resonance imaging (MRI) device or an external computed tomography (CT) device.

6. The image registration device of claim 1, wherein the first feature point and the second feature point comprise areas corresponding to at least one of a portal vein, a branch of a blood vessel, and a tumor of the object.

7. An image registration method comprising:
    periodically acquiring an ultrasonic image, by using a probe, of an object;
    acquiring a medical image of the object, the medical image having a different modality from the ultrasonic image;
    determining position information of the probe corresponding to each of pre-acquired ultrasonic images, based on information about a point in time at which each of the pre-acquired ultrasonic images is acquired, and information about a point in time at which the position information of the probe is acquired;
    storing the pre-acquired ultrasonic images and the position information of the probe corresponding to each of the pre-acquired ultrasonic images;
    displaying the medical image and the pre-acquired ultrasonic images on a display screen;
    receiving an input selecting a first feature point of the medical image, and receiving an input selecting a second feature point of a first ultrasonic image among the stored pre-acquired ultrasonic images; and
    registering the first ultrasonic image and the medical image, based on the first feature point of the medical image, the second feature point of the first ultrasonic image, and the position information of the probe corresponding to the first ultrasonic image.

8. The image registration method of claim 7, further comprising:
    instructing a user to scan a certain area of the object by using the probe.

9. The image registration method of claim 7, further comprising:

storing a plurality of ultrasonic images, sectional images in the medical image, which are registered to the plurality of ultrasonic images, respectively, and the position information of the probe corresponding to each of the plurality of ultrasonic images; and re-registering the ultrasonic image and the medical image based on a third feature point of a first sectional image of the sectional images, a fourth feature point of a second ultrasonic image of the plurality of ultrasonic images, and the position information of the probe corresponding to the second ultrasonic image.

10. The image registration method of claim 7, wherein the position information of the probe comprises information of at least one of a position, a direction, a tilt, and a rotation angle.

11. The image registration method of claim 7, wherein the medical image comprises a three-dimensional volume image acquired from an external magnetic resonance imaging (MRI) device or an external computed tomography (CT) device.

12. The image registration method of claim 7, wherein the first feature point and the second feature point comprise areas corresponding to at least one of a portal vein, a branch of a blood vessel, and a tumor of the object.

13. A non-transitory computer-readable recording method having recorded thereon a computer program for executing the method of claim 7.

* * * * *